United States Patent [19]

Burba et al.

[11] Patent Number: 5,155,182

[45] Date of Patent: Oct. 13, 1992

[54] IMIDAZOLYL DERIVATIVES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING SAID IMIDAZOLYL DERIVATIVES

[75] Inventors: Christian Burba, Herbern; Werner Mrotzek, Dortmund, both of Fed. Rep. of Germany

[73] Assignee: Schering AG, Bergkamen, Fed. Rep. of Germany

[21] Appl. No.: 561,791

[22] Filed: Aug. 2, 1990

[30] Foreign Application Priority Data

Sep. 14, 1989 [DE] Fed. Rep. of Germany ....... 3930718

[51] Int. Cl.$^5$ .................. C08G 59/40; C08G 65/00
[52] U.S. Cl. .................. 525/526; 525/531; 528/094; 528/111; 528/117; 548/313.7; 548/336.1; 548/338.1; 548/340.1; 548/312.7; 548/335.5; 252/182.26
[58] Field of Search .......... 525/526, 531; 528/94, 528/111, 117; 548/336, 341; 252/182.26

[56] References Cited

U.S. PATENT DOCUMENTS

| | | | |
|---|---|---|---|
| 3,489,695 | 1/1970 | Green | 528/117 |
| 3,756,984 | 9/1973 | Klaren et al. | 528/94 |
| 4,066,625 | 1/1978 | Bolger | 528/94 |
| 4,358,571 | 11/1982 | Kaufman et al. | 528/117 |
| 4,420,605 | 12/1983 | Kaufman | 528/94 |

Primary Examiner—John C. Bleutge
Assistant Examiner—Frederick Krass
Attorney, Agent, or Firm—Curtis, Morris & Safford

[57] ABSTRACT

The invention relates to new imidazolyl derivatives, their use as curing agents in epoxy-resin compositions, and curable epoxy-resin compositions containing them and composed of an epoxy resin and compounds of the general formula

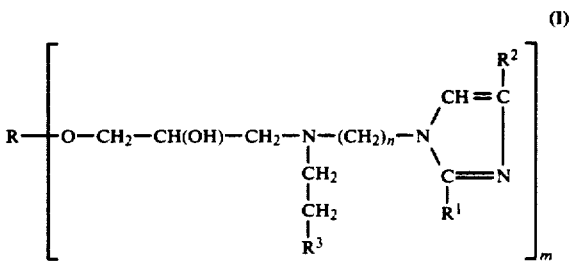

(I)

where R is the group of the alcohol component used to produce the glycidyl ethers, $R^1$ and $R^2$ are, independently of each other, hydrogen, $-CH_3$ or $-C_2H_5$, n is 2 or 3, $R^3$ is COOH, $-CH$, $-COHN-N_{H_2}$, $-COOCH_2-CH_2-OH$ or $COOR^4$, $R^4$ being an aliphatic hydrocarbon group having from 1 to 4 carbon atoms, and m is equal to the valence of R.

24 Claims, No Drawings

IMIDAZOLYL DERIVATIVES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING SAID IMIDAZOLYL DERIVATIVES

The invention relates to new imidazolyl derivatives, to their use as curing agents in epoxy-resin compositions, and to curable epoxy-resin compositions comprising an epoxy resin and the compounds of general formula (I), and optionally conventionally used curing agents and solvents, for the manufacture of molded articles.

In the manufacture of composite materials, two basic processes are employed today. One of these is the wet lay-up process in which the reinforcing materials are impregnated with the curable mixture and heat-cured in one step to the thermoset final state.

In the other process, the two-step process, so-called prepregs ar first produced from the reinforcing materials and the curable mixture, and these prepregs are then processed into finished parts in a separated second step. With respect to operating procedure, a distinction is made between working with solvents and working without solvents.

The prepregs are normally produced in a continuous process in which the reinforcing materials are passed through an impregnating bath of the resin/curing agent mixture being used or the impregnant is mixed only just before it is applied to the base material and then spread thereon with a special device. The amount of impregnant to be applied to a given base-material web is controlled not only through the viscosity of the impregnant but also through squeeze rolls located downstream.

With solvent-containing systems, the solvent contained in the impregnating solution is evaporated through input of heat after the impregnating operation and the resin system is converted at the same time from the A stage to the B stage. Depending on the process conditions and the resin system used, the reinforcing materials impregnated with liquid to highly viscid impregnant are thus turned into a prepreg that is slightly tacky to almost dry. In this process step it is important that the solvent is completely eliminated from the impregnating mixture and that the latent curing agent needed to cure the prepreg in the second process step is not activated just jet as this would cause the impregnated reinforcing materials to react completely, which is not desired.

With solvent-free systems, depending on the chemical composition of the resin system the material either also undergoes a short heat treatment after impregnation or the reinforcing materials are lined on both sides with release sheets immediately after impregnation, without any separate heat treatment, and placed into intermediate storage appropriate to the system. During this intermediate storage, either a gradual transition of the resin system to the B stage takes place or the impregnant is fixed on the base materials through physical effects alone and largely without chemical changes.

The prepregs so obtained can be stored and shipped as rolls before they are cut to size and stacked to the thickness of the finished part, as required by the intended end use. Under the simultaneous action of pressure and heat, the prepreg stack is completely cured to give a high-strength molded part, the still fluid low-molecular-weight resins thus being converted to the high-molecular-weight C stage of a thermoset.

While in the one-step process long open times and short cure times at low cure temperatures are required, prolonged storage stability of the prepregs is an additional requirement in the two-step process. Storage temperatures lower than room temperature have become steadily less acceptable in practice.

Of importance is further that depending on the prepreg manufacturing method the viscosity of the ready-to-use curable mixture remain substantially constant for as long a period as possible. This is necessary, especially when an impregnating bath of large volume is used, for achieving constant resin deposition and a constant B stage since the manufacturing conditions cannot be continually adjusted to changing relationships within the curable mixture and since fluctuations in the viscosity have an adverse effect on the physical properties of the fully cured end product.

What is desired in practice is a curable mixture whose viscosity remains constant in the impregnating bath for an extended period and which can then be stored as a prepreg at room temperature for a long time without undergoing chemical changes.

Regardless of how they are manufactured, the prepregs should cure completely within a short time at the lowest possible temperature, the maximum temperature of the exothermic reaction should remain at a low level even with moderately thick layers, and the profile of physical properties of the finished products should meet practical requirements.

These requirements involving curing behavior and profile of properties apply also to epoxy-resin systems to be processed by the wet lay-up method.

Dicyandiamide, long used as a latent curing agent in curable mixtures based on epoxy resins, is usually combined with co-curing agents and/or accelerators to obtain the desired properties. A great many suggestions for its used in this field are known from the literature.

While dicyandiamide solutions can be used to produce homogeneous substrates, the use of solvents gives rise to other problems.

Dicyandiamide is soluble in sufficient amounts in only a few solvents, particularly dimethylformamide and methyl glycol. However, these solvents are toxicologically hazardous and create problems both in the manufacture of the prepregs, that is, during impregnation of the reinforcing materials and conversion to the B stage, and in waste disposal.

Since dicyandiamide is only sparingly soluble, rather large amounts of solvents must be used, and these affect the impregnating viscosity in such a way that the binder content on the reinforcing materials cannot be chosen as desired.

Since these solvents cannot be removed completely during the cure, there is, moreover, the danger than when the finished parts are subjected to thermal loading the material will fail prematurely and/or the solvents will be given off uncontrolled to the ambient air in the field.

When solid crystalline dicyandiamide is used without solvents in liquid epoxy resins, the dicyandiamide should be dispersed directly in the requisite amount of epoxy resin, or a highly filled dicyandiamide/epoxy resin paste should first be prepared and later adjusted with the bulk of the epoxy resin to the desired resin/curing agent concentration.

In any event, the preparation of the dispersions here is not a simple matter. Moreover, when standing for an extended period of time, particularly under impregnating conditions, the dispersions tend to separate.

When solid crystalline dicyandiamide is used without solvents in epoxy resins which at room temperature are solid, a paste of dicyandiamide and liquid epoxy resins should again be made first and then worked into the solid-resin melt at elevated temperature.

Apart from the problems mentioned, undesired amounts of liquid epoxy resins are incorporated in the solid resin when this operating procedure is employed.

Moreover, when solid crystalline dicyandiamide is used, inhomogeneities due to undissolved and unreacted particles are observed in the cured substrates.

The object of the present invention is to overcome the drawbacks of the prior art and provide curable mixtures, based on epoxy compounds and liquid latent curing agents soluble or homogeneously dispersable in the epoxy resins, which cure to the thermoset final state at relatively low temperatures within a short time and without high peak exotherms, whose heat resistance meets practical requirements, and which in prepregs have adequate storage stability at room temperature.

This object is accomplished through the use of a new curing agent, optionally with the concurrent use of conventional latent curing agents.

The invention thus relates to compounds of the general formula

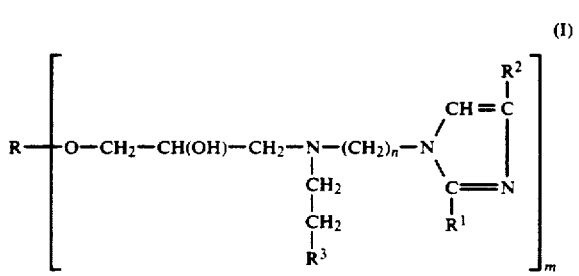
(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, $-CH_3$ or $-C_2H_5$, n is 2 or preferably 3, $R^3$ is COOH, $-CN$, $-CONH-NH_2$, $-COOCH_2-CH_2-OH$ or $COOR^4$, $R^4$ being an aliphatic hydrocarbon group having from 1 to 4 carbon atoms, and particularly $-CH_3$, or $-C_2H_5$, and m is equal to the valence of R, and preferably between 1 and 3.

The invention further relates to the use of compounds of the general formula

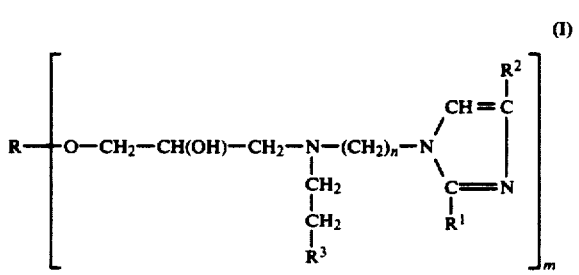
(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, $-CH_3$ or $-C_2H_5$, n is 2 or preferably 3, $R^3$ is COOH, $-CN$, $-CONH-NH_2$, $-COOCH_2-CH_2-OH$ or $COOR^4$, $R^4$ being an aliphatic hydrocarbon group having from 1 to 4 carbon atoms, and particularly $-CH_3$, or $-C_2H_5$, and m is equal to the valence of R, and preferably between 1 and 3, optionally with the concurrent use of commonly used nitrogen-containing heterocyclic amino compounds as curing agents for epoxy resins.

The invention further relates to curable epoxy-resin compositions comprising (a) an epoxy resin with more than one epoxy group per molecule on the average;

(b) compounds of the general formula

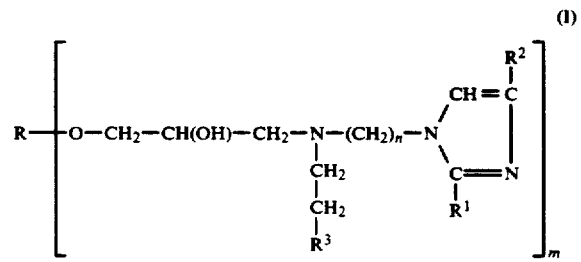
(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, $-CH_3$ or $-C_2H_5$, n is 2 or preferably 3, $R^3$ is COOH, $-CN$, $-CONH-NH_2$, $-COOCH_2-CH_2-OH$ or $COOR^4$, $R^4$ being an aliphatic hydrocarbon group having from 1 to 4 carbon atoms, and particularly $-CH_3$, or $-C_2H_5$, and m is equal to the valence of R, and preferably between 1 and 3; optionally (c) conventionally used solvents, fillers, reinforcements or embedments, pigments and auxiliaries; and optionally (d) conventionally used nitrogen-containing heterocyclic amino compounds.

The invention further relates to curable epoxy-resin compositions wherein the reinforcements or embedments are impregnated at room temperature with the binder, composed of (a) an epoxy resin with more than one epoxy group per molecule on the average;

(b) compounds of the general formula

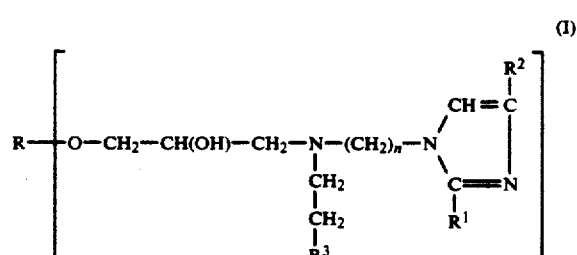
(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, $-CH_3$ or $-C_2H_5$, n is 2 or preferably 3, $R^3$ is COOH, —CN, —CONH—$NH_2$, —COOCH$_2$—$CH_2$—OH or COO$R^4$, $R^4$ being an aliphatic hydrocarbon group having from 1 to 4 carbon atoms, and particularly —$CH_3$, or —$C_2H_5$, and m is equal to the valence of R, and preferably between 1 and 3; optionally (c) conventionally used solvents, fillers, reinforcements or embedments, pigments and auxiliaries; and optionally (d) conventionally used nitrogen-containing heterocyclic amino compounds, and optionally converted at elevated temperature to the semisolid but still fusible state (B stage).

The invention further relates to molded epoxy-resin articles characterized in that in a first step the reinforcements or embedments are impregnated at room temperature with the binder, composed of (a) an epoxy resin with more than one epoxy group per molecule on the average;

(b) compounds of the general formula

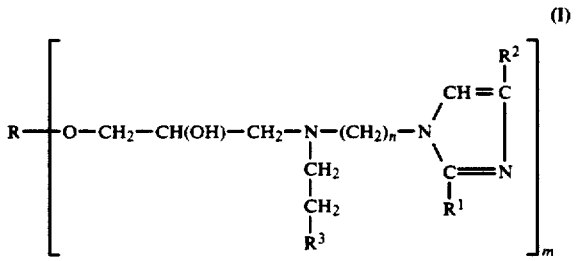

(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, —$CH_3$ or —$C_2H_5$, n is 2 or preferably 3, $R^3$ is COOH, —CN, —CONH—$NH_2$, —COOCH$_2$—$CH_2$—OH or COO$R^4$, $R^4$ being an aliphatic hydrocarbon group having from 1 to 4 carbon atoms, and particularly —$CH_3$, or —$C_2H_5$, and m is equal to the valence of R, and preferably between 1 and 3; optionally (c) conventionally used solvents, fillers, reinforcements or embedments, pigments and auxiliaries; and optionally (d) conventionally used nitrogen-containing heterocyclic amino compounds, and optionally converted to the semisolid but still fusible state (B stage), and that in a second step the wet laminates or prepregs are molded or placed between substrates to be bonded and with the use of pressure completely cured at elevated temperature.

The imidazolyl compounds of the invention can be prepared by simple addition reactions, a glycidyl ether containing ether groups being reacted in a first step with N-aminoalkylimidazolyl compounds containing primary amino groups, in a ratio of epoxy groups to primary amino groups of about 1:1, and acrylic acid or its derivatives being added in a second step to the secondary amino groups formed. The addition reactions of the first and second steps are carried out by known procedures.

The glycidyl ethers containing ether groups used in accordance with the invention to prepare the imidazolyl compounds are products of the reaction of mono- or polyhydric alcohols and epichlorohydrin to give chlorohydrin ethers followed by ring formation with alkali metal hydroxides. These reactions are carried out by methods which are part of the known prior art.

In place of the alcohols, their higher-molecular-weight secondary products containing ether or ester groups may here be used.

As a rule, polyether polyols are used which are obtained through anionic polymerization, copolymerization and block copolymerization of alkylene oxides such as ethylene oxide, propylene oxide and butylene oxide with mono-, di- or polyfunctional alcohols, such as 1,4-butanediol, 1,1,1-trimethylolethane, 1,1,1-trimethylolpropane, 1,2,6-hexanetriol, glycerol, pentaerythritol and sorbitol, or with amines, such as methylamine, ethylenediamine and 1,6-hexamethylenediamine, as starting components or through cationic polymerization and copolymerization of cyclic ethers such as tetrahydrofuran, ethylene oxide and propylene oxide with acid catalysts such as boron trifluoride etherate, and through polycondensation of glycols which are polycondensable with dehydration, such as 1,6-hexanediol, in the presence of acid etherification catalysts such as paratoluenesulfonic acid, and, in view of their flame-retardant effect, products of oxyalkylation of phosphoric acid and phosphorous acids with ethylene oxide, propylene oxide, butylene oxide or styrene oxide, for example. Appropriate polythioether polyols are mainly the products of polycondensation of thioglycol with itself and with diols and/or polyols, such as 1,6-hexanediol, triethylene glycol, 2,2-dimethyl-1,3-propanediol and 1,1,1-trimethylolpropane, in the presence of acid etherification catalysts such as phosphoric acid and phosphorous acid. Suitable polyacetals are mainly the polycondensation products of formaldehyde and diols and/or polyols, such as diethylene glycol, triethylene glycol, 1,4-butanediol, 1,6-hexanediol, thioglycol and 1,1,1-trimethylolpropane, with acid catalysts such as phosphoric acid and para-toluenesulfonic acid. Appropriate polyester polyols are mainly the condensation products with di- and/or polycarboxylic acids and di- and/or polyols obtained by polycondensation of adipic acid, phthalic acid, tetrahydrophthalic acid or hexahydrophthalic acid and ethylene glycol, 1,4-butanediol, diethylene glycol, triethylene glycol, 1,6-hexanediol or 2,2-dimethyl-1,2,6-propanediol, as well as polycarbonates of the aforesaid di- and polyols and polyester amides with the additional use of amino alcohols such as alpha-caprolactone.

The starting alcohols have molecular weights of about 100 to 2,000. In accordance with the invention, polypropylene glycols with molecular weights of about 500 to 1,000 are preferred.

The imidazolyl compounds used in accordance with the invention are compounds of the general formula

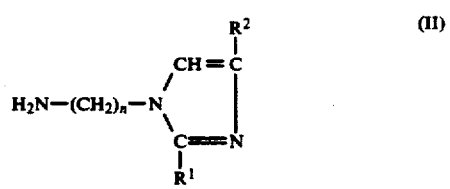

(II)

where $R^1$ and $R^2$ are, independently of each other, aliphatic or aromatic hydrocarbon groups, and particularly H, —$CH_3$ or —$C_2H_5$ and n is 2 or preferably 3. One mol of the imidazolyl compound is used per epoxy group of the aforesaid glycidyl compounds.

The acrylic acid or acrylic acid derivatives which in accordance with the invention are also used are compounds of the general formula $$CH_2=CH-R^3 \quad (III)$$

where $R^3$ is —COOH, —CN, —CONH—NH$_2$, —COOC$_2$H$_4$OH or —COOR$^4$, $R^4$ being an aliphatic hydrocarbon group having from 1 to 4 carbon atoms, and particularly —CH$_3$ or —C$_2$H$_5$.

One mol of the acrylic acid compound is used per secondary amino group of the addition compounds prepared in the first step.

The addition products which in accordance with the invention can be prepared by these process steps are compounds of the general formula

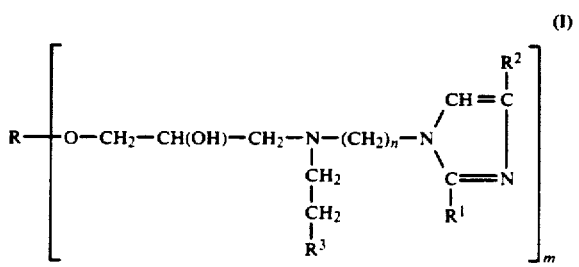

(I)

where R is the group of the alcohol component used to produce the glycidyl ethers, and more particularly the polypropylene glycol group with a molecular weight of from 500 to 1,000, $R^1$ and $R^2$ are, independently of each other, hydrogen, —CH$_3$ or —C$_2$H$_5$ and n is 2 or preferably 3, $R^3$ is COOH, —CN, —CONH—NH$_2$, —COOCH$_2$—CH$_2$—OH or COOR$^4$, $R^4$ being an aliphatic hydrocarbon group having from 1 to 4 carbon atoms, and particularly —CH$_3$, or —C$_2$H$_5$, and m is equal to the valence of R, and preferably between 1 and 3.

The curing agents of the invention may be used alone or as a mixture at the rate of from 5 to 35 g, and more particularly from 7 to 25 g, but preferably from 10 to 20 g, of curing agent per 100 g of epoxy resin.

The compounds of the general formula (I) may also be used in the form of their salts. Use may here be made of the organic and inorganic salt formers known in this field. In accordance with the invention, however, the mono- or polybasic organic carboxylic acids are preferred, the branched-chain monocarboxylic acids having up to 10 carbon atoms, such as 2-ethylhexoic acid, being particularly well suited.

The epoxy resins which in accordance with the invention are used as a constituent of the binder are glycidyl esters and ethers with two or more epoxy groups per molecule, and preferably the glycidyl ethers based on mono- or polyhydric phenols. In accordance with the invention, glycidyl ethers of 2,2-bis(4-hydroxyphenyl)propane (bisphenol A) with epoxide values of from 0.2 to 0.6, and particularly the compounds with epoxy values of from 0.45 to 0.55 which are liquid at room temperature, are preferred. The glycidyl ethers based on bisphenol F and the novolacs have also proved advantageous.

Also usable are the commercial halogenated, and more particularly brominated, epoxy resins based on the aforesaid phenols.

The amino compounds which in accordance with the invention may also be used are preferably commonly used nitrogen-containing heterocyclic amino compounds, that is, N-alkylimidazoles such as N-methyl- or N-ethylimidazole and/or imidazoline compounds of the general formula

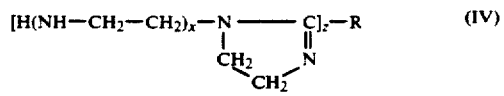

where Q is an optionally branched alkyl or alkylene group having fewer than 10 carbon atoms, and particularly —CH$_3$, —CHOH—CH$_3$ or —(CHR')$_y$, R' being H or —CH$_3$, x being 1, 2 or 3, y being 4 to 8, and z being equal to the valence of Q, and particularly those where x is 1, z is 1 and R is —CH$_3$ or —CH$_2$—CH$_3$. Other curing agents commonly used in this field may be used concurrently, if desired.

For modifications of the properties of the end product, other epoxy resins may be used concurrently, as may modifiers or auxiliaries such as phenolic resins, melamine resins, silicone resins, inorganic and organic fillers such as quartz powders, titanium dioxide, carbon black, and silicone or butadiene rubber.

To obtain the desired viscosity, resins of different viscosities, diluents, or such conventionally used solvents as dimethyl formamide, acetone, methyl ethyl ketone, methyl glycol or propylene glycol monomethyl ether or mixtures thereof may be used.

In prepregging, organic and inorganic fibers, nonwoven and woven fabrics based on aramid, carbon or cellulose, metals such as boron, steel, etc., ceramics and especially glass are used.

The solvent-containing prepregs are made by the known method in which the base materials are impregnated with the reactive resin mixture in an impregnating bath and, after the excess resin has been squeezed off, continuously converted from the A stage to the B stage with input of energy (mostly heat) and simultaneous elimination of the solvent. Depending on the desired prepreg consistency (viscid to solid), the prepregs are then provided on both sides with a release sheet and wound into a roll for storage and shipping. The further processing involves cutting the individual prepreg layers to size and assembling them into a stack from which a highly crosslinked part is produced by shaping with simultaneous heat input.

The curing agents of the invention can also be used successfully in solventless systems based on epoxy resins and, optionally, conventionally used curing agents. Here the base materials are impregnated at optionally elevated temperature and by conventional methods with the binder system and placed into storage appropriate to the system before they are processed further like the solvent-containing systems.

Further examples for solventless systems are wet lay-up laminates, base materials for the electrical industry, fiber-reinforced molded parts produced in situ, heat-curing one-component adhesives for the bonding of body sections in the automotive industry (flange-joint adhesives), for example, as well as epoxy-resin castings, epoxy-resin coatings and epoxy-resin filament- or tape-wound structures.

EXAMPLES

(I) Preparation of the Curing Agents of the Invention

Example 1

(a) 125 g (1 mol) of 1-(3-aminopropyl)imidazole is introduced as initial charge under nitrogen, preheated to about 70° C., and slowly mixed with 475 g of the diglycidyl ether of polypropylene glycol 620 (epoxide equivalent 475). After the exothermic reaction has subsided, stirring is continued for 2 hr. at 70° C.

(b) To the adduct produced under (a), 86 g (1 mol) of methyl acrylate is added at about 50° C. and stirring is continued for about 2½ hr. at 60° C.

(c) To the addition product described under (b), 62.5 g of 80% hydrazine hydrate in water (corresponding to 1 mol of hydrazine) is added at 50°-60° C. and stirring is continued for 2 hr. at 70° C. The batch is then heated to 90° C., and after 1 hr. at 90° C. a vacuum of up to about 10 mbar is carefully applied to remove water and methanol.

Characteristics: Amine value: 226-224.
Viscosity: 38.0 Pa·s/25° C.

Example 2

(a) 125 g (1 mol) of 1-(3-aminopropyl)imidazole is introduced as initial charge under nitrogen, preheated to about 70° C., and slowly mixed with 475 g of the diglycidyl ether of polypropylene glycol 620 (epoxide equivalent 475). After the exothermic reaction has subsided, stirring is continued for 2 hr. at 70° C.

(b) To the adduct produced under (a), 116 g (1 mol) of 2-hydroxyethyl acrylate is added and stirring is continued for about 2½ hr. at 60° C.

Characteristics: Amine value: 144-145.
Viscosity: About 22.0 Pa·s/25° C.

Example 3

The same procedure is used as in Example 1 (a), (b) and (c) except that in place of 475 g of the diglycidyl ether of polypropylene glycol 620 158 g of hexanediol diglycidyl ether (epoxide equivalent 158) is used.

Characteristics: Amine value: 265-268.
Viscosity: About 14.5 Pa·s/25° C.

Example 4

(a) 125 g (1 mol) of 1-(3-aminopropyl)imidazole is introduced as initial charge under nitrogen, preheated to about 70° C., and slowly mixed with 714 g of the triglycidyl ether of trifunctional polypropylene glycol (epoxide equivalent 714). After the exothermic reaction has subsided, stirring is continued for 2 hr. at 70° C.

(b) To the adduct produced under (a), 86 g (1 mol) of methyl acrylate is added at about 50° C. and stirring is continued for about 2½ hr. at 60° C.

Characteristics: Amine value: 114-115.
Viscosity: About 3.5 Pa·s/25° C.

Example 5

To 160 g of the addition product described in Example 2 32 g of 2-ethylhexoic acid is added and a homogeneous mixture is produced by stirring at room temperature.

Characteristics: Amine value: 121.
Viscosity: 14.3 Pa·s/25° C.

(II) (a) Preparation of a Solvent-Containing Prepreg Reaction Mixture

Example 1

A solution of 14 g of the curing agent of (I) Example 1 and 20 g of methyl ethyl ketone, prepared at room temperature, is mixed with 100 g of an epoxy resin based on bisphenol A* epoxide equivalent about 190, and the curing characteristics of this system are determined by differential scanning calorimetry (DSC) using a TA 3000 unit manufactured by Mettler equipped with a DSC 30 measuring cell.

*epoxide equivalent about 190

To this end, about 25 mg of the reaction mixture are weighed into an aluminum crucible and, starting from 20° C., heated at the rate of 10° C./min. while flushing with nitrogen. In addition to the activation temperature, the temperature at which the maximum evolution of heat occurs (the peak temperature) and the quantity of heat liberated during the reaction are determined. The activation temperature serves, among other things, as a measure of the maximum permissible thermal load during the evaporation of the solvent (without the curing reaction appreciably setting in) and should not be too low, in the interest of as complete removal of the solvent as possible. The peak temperature determines the temperature level necessary for the cure of the material and for processing reasons should not be too high but close to the activation temperature. To prevent excessive thermal loading of the material during the cure, and to avoid large temperature gradients, the exotherm produced during the reaction should not be too high, either.

The values determined on the basis of Example 1 are presented in Table 1. The values listed in Table 1 for the other examples have been determined in the same manner as those of Example 1.

The comparative example relates to a standard prepreg reaction mixture with a curing agent of the following composition:

8 g dicyandiamide (as latent curing agent)
2 g N-methylimidazole (as accelerator)

TABLE 1

Reaction-specific data on various solvent-containing prepreg reaction mixtures based on differential scanning calorimetry

| Example | 1 | 2 | 3 | 4 | Comparative example |
|---|---|---|---|---|---|
| Curing agent | (I) 1 | (I) 2 | (I) 3 | (I) 4 | Dicyandiamide N-methylimidazole |
| Activation temperature °C. | 105 | 110 | 95 | 115 | 100 |
| Peak temperature °C. | 141 | 140 | 135 | 148 | 148 |
| Exothermicity ΔH, J/g | 288 | 260 | 370 | 152 | 354 |

(II) (b) Preparation of a solventless prepreg reaction mixture

EXAMPLE 1 1

100 g of an epoxy resin (epoxide equivalent about 190) is mixed with 7 g of the inventive reaction product (I) 1 and used to make prepregs. This mixture has a viscosity at room temperature of 11.0 Pa.s and is workable even after 10 hours.

The prepregs are formed on the laboratory scale by spreading the reaction mixture onto a glass-filament fabric in a satin weave, measuring about 0.1 m², which after impregnation is lined on both sides with release sheets and then stored at room temperature.

After 24-hour storage at room temperature, the material has aged sufficiently to be processed as a slightly tacky prepreg in several layers by the hot-press molding method at 0.1 bar and temperatures of from 100° to 120° C., in from 30 minutes to 1 hour, into high-strength molded articles. The end product, fully cured in this manner, exhibits no flaws of any kind with regard to the adhesion of the individual prepreg layers.

The storage-stability values given in Table 2 are determined on the basis of conditions similar to those used in actual practice. The impregnated fabric is stored between two polyethylene sheets at 23° C. under standard climatic conditions. A layer of a specimen is molded at 24-hour intervals under conditions duplicating those used in practice (1 hr, 120° C., 0.1 bar). The storage-stability value indicated is based on the last day on which the resin is fluid. The other storage-stability values given in Table 2 are determined in the same way.

TABLE 2

| | Storage stability of solventless prepregs | | | |
|---|---|---|---|---|
| Example | Curing agent Example | Curing agent, g | 100 g of epoxy resin | Storage stability (day) |
| 1 | (I) 1 | 7 | Bisphenol A, epoxy value 0.53 | >21 |
| 2 | (I) 1 | 14 | Bisphenol A, epoxy value 0.53 | 8 |
| 3 | (I) 1 | 28 | Bisphenol A, epoxy value 0.53 | 6 |
| 4 | (I) 2 | 7 | Bisphenol A, epoxy value 0.53 | >21 |
| 5 | (I) 2 | 14 | Bisphenol A, epoxy value 0.53 | >35 |
| 6 | (I) 2 | 28 | Bisphenol A, epoxy value 0.53 | >21 |

TABLE 2-continued

| | Storage stability of solventless prepregs | | | |
|---|---|---|---|---|
| Example | Curing agent Example | Curing agent, g | 100 g of epoxy resin | Storage stability (day) |
| 7 | (I) 3 | 14 | Bisphenol A, epoxy value 0.53 | >28 |
| 8 | (I) 4 | 14 | Bisphenol A, epoxy value 0.53 | >28 |

(III) Determination of Influence of Curing Agent

To determine the properties of the curing agent as a function of structure, the mixtures, composed only of epoxy resin and curing agent so as to eliminate any distorting influences of reinforcements and additives, are cured and tested.

In the examples listed in Table 3, a glycidyl ether based on bisphenol A and having an epoxy value of 0.53 is used as epoxy resin.

To produce the test specimens, 100 g of epoxy resin is mixed in each case at room temperature with the quantity of curing agent indicated in Table 3 and cured in a steel mold under the conditions stated to give flat molded parts 4 mm thick. From these molded parts, test specimens are then taken by sawing or milling. On these specimens, the properties specified in Table 3 are determined in conformity with the test standards listed below.

| | | Test-specimen dimensions |
|---|---|---|
| Flexural strength | DIN 53,452 | 80 × 10 × 4 mm³ |
| Deflection | DIN 53,452 | 80 × 10 × 4 mm³ |
| Impact strength | DIN 53,453 | 50 × 6 × 4 mm³ |
| Tensile strength | DIN 53,455 | Dumbbell No. 3 |
| Elongation | DIN 53,455 | Dumbbell No. 3 |
| Modulus of elasticity | DIN 53,457 | Dumbbell No. 3 |
| Heat distortion temperature | DIN 53,461 | 120 × 10 × 4 mm³ |

TABLE 3

| Thermal and mechanical properties | | | | |
|---|---|---|---|---|
| Example | 1 | 2 | 3 | 4 |
| Curing agent | (I) 1 | (I) 1 | (I) 1 | (I) 1 |
| Curing agent, g | 7 | 14 | 14 | 14 |
| Curing conditions | 2h/120° C. | 2h/80° C. | 2h/100° C. | 2h/120° C. |
| Flexural strength | 65 | 68 | 58 | 49 |
| Deflection | 4.8 | 5.9 | 5.6 | 5.4 |
| Impact strength | 6 | 4 | 3 | 3 |
| Tensile strength | 22 | 39 | 29 | 30 |
| Elongation | 0.7 | 1.5 | 1.2 | 1.3 |
| Modulus of elasticity | 3250 | 3040 | 2460 | 2330 |
| Heat distortion temp. | 89 | 77 | 114 | 122 |
| Example | 5 | 6 | 7 | 8 |
| Curing agent | (I) 2 | (I) 2 | (I) 2 | (I) 2 |
| Curing agent, g | 7 | 10 | 14 | 14 |
| Curing conditions | 2h/120° C. | 2h/120° C. | 2h/80° C. | 2h/100° C. |
| Flexural strength | 119 | 89 | 93 | 85 |
| Deflection | 9.5 | 6.7 | 11.5 | 10.2 |
| Impact strength | 14 | 17 | 16 | 13 |
| Tensile strength | 74 | 29 | 41 | 29 |
| Elongation | 3.4 | 1.5 | 1.6 | 1.3 |
| Modulus of elasticity | 3030 | 1680 | 2730 | 2410 |
| Heat distortion temp. | 70 | 109 | 88 | 107 |
| Example | 9 | 10 | 11 | 12 |
| Curing agent | (I) 2 | (I) 3 | (I) 4 | (I) 5 |
| Curing agent, g | 14 | 14 | 14 | 14 |
| Curing conditions | 2h/120° C. | 2h/120° C. | 2h/120° C. | 2h/120° C. |
| Flexural strength | 59 | 91 | 85 | 86 |
| Deflection | 6.0 | 7.9 | 12.9 | 14 |

TABLE 3-continued

| | Thermal and mechanical properties | | | |
|---|---|---|---|---|
| Impact strength | 4 | 14 | 13 | 17 |
| Tensile strength | 28 | 64 | 26 | 57 |
| Elongation | 1.2 | 3.8 | 1.1 | 4.0 |
| Modulus of elasticity | 2360 | 2430 | 2430 | 2290 |
| Heat distortion temp. | 120 | 122 | 101 | 108 |

We claim:

1. A compound of the formula (I)

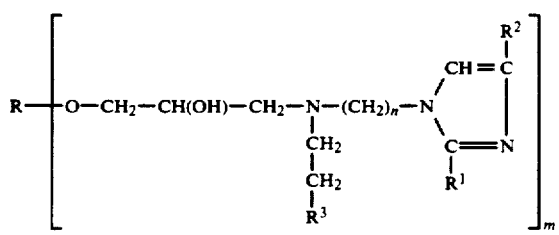

wherein R is a di- or polyfunctional radical left by removal of hydroxyl groups from a diol or polyol, $R^1$ and $R^2$ are, independently of each other, hydrogen, —$CH_3$ or $C_2H_5$, n is 2 or 3, $R^3$ is COOH, —CN, —CONH—$NH_2$, —COOCH$_2$—CH$_2$—OH or —COOR$^4$, $R^4$ being an aliphatic hydrocarbon group having from 1 to 4 carbon atoms, and m is equal to the valence of R.

2. A curing agent for an epoxy-resin composition, which agent comprises a compound as claimed in claim 1.

3. A curing agent according to claim 2, further comprising a nitrogen-containing heterocyclic amino compound of the formula

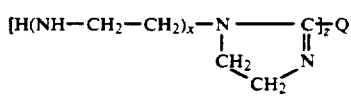

wherein Q is an unbranched or branched alkyl or alkylene group having 1 to 9 carbon atoms, x is 1, 2 or 3, and z is equal to the valence of Q.

4. A curable epoxy-resin composition comprising
 (a) an epoxy resin having on the average more than one epoxy group per molecule; and
 (b) a compound of the formula (I)

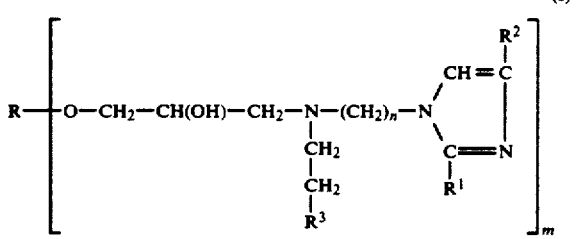

wherein R is a di- or polyfunctional radical left by removal of hydroxyl groups from a diol or polyol, $R^1$ and $R^2$ are, independently of each other, hydrogen, —$CH_3$ or $C_2H_5$ and n is 2 or 3, $R^3$ is COOH, —CN, —CONH-NH$_2$, —COOCH$_2$—CH$_2$—OH or —COOR$^4$, $R^4$ being an aliphatic hydrocarbon group having from 1 to 4 carbon atoms, and m is equal to the valence of R.

5. A curable epoxy-resin composition according to claim 4, further comprising a solvent, filler, reinforcement or embedment, pigment or auxiliary.

6. A curable epoxy-resin composition according to claim 4, further comprising a nitrogen-containing heterocyclic amino compound of the formula

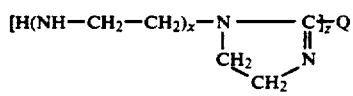

wherein Q is an unbranched or branched alkyl or alkylene group having 1 to 9 carbon atoms, x is 1, 2 or 3, and z is equal to the valence of Q.

7. A curable epoxy-resin composition comprising a reinforcement or embedment impregnated with a binder containing
 (a) an epoxy resin having on the average more than one epoxy group per molecule; and
 (b) a compound of the formula (I)

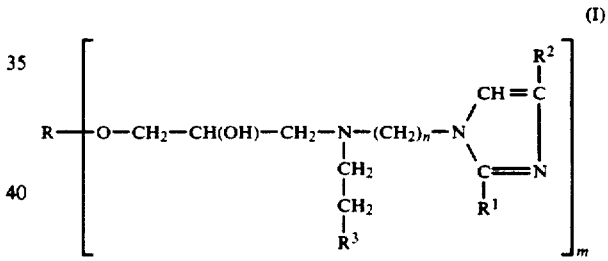

wherein R is a di- or polyfunctional radical left by removal of hydroxyl groups from a diol or polyol, $R^1$ and $R^2$ are, independently of each other, hydrogen, —$CH_3$ or $C_2H_5$, n is 2 or 3, $R^3$ is COOH, —CN, —CONH-NH$_2$, —COOCH$_2$—CH$_2$—OH or —COOR$^4$, $R^4$ being an aliphatic hydrocarbon group having from 1 to 4 carbon atoms, and m is equal to the valence of R.

8. A curable epoxy-resin composition according to claim 7, further comprising a solvent, filler, reinforcement or embedment, pigment or auxiliary.

9. A curable epoxy-resin composition according to claim 7, further comprising a nitrogen-containing heterocyclic amino compound of the formula

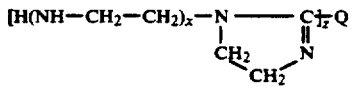

wherein Q is an unbranched or branched alkyl or alkylene group having 1 to 9 carbon atoms, x is 1, 2 or 3, and z is equal to the valence of Q.

10. A curable epoxy-resin composition according to claim 7 that is converted at elevated temperature to a semisolid but fusible state (B stage).

11. A curing agent according to claim 2, wherein the compound of the formula (I) is in the form of a salt with an organic or inorganic acid.

12. A curing agent according to claim 11, wherein the organic acid is a branched-chain monocarboxylic acid having up to 10 carbon atoms.

13. A compound according to claim 1, wherein R together with the hydroxyl group has a molecular weight of 100 to 2000.

14. A compound according to claim 1, wherein the diol or polyol is selected from the group consisting of a polyether polyol, a polythioether polyol, a polyacetal polyol and a polyester polyol.

15. A compound according to claim 1, wherein the diol or polyol is polypropylene glycol having a molecular weight of about 500 to 1000.

16. A curing agent according to claim 1, wherein R together with the hydroxyl groups has a molecular weight of 100 to 2000.

17. A curing agent according to claim 2, wherein the diol or polyol is selected from the group consisting of a polyether polyol, a polythioether polyol, a polyacetal polyol and a polyester polyol.

18. A curing agent according to claim 2, wherein the diol or polyol is polypropylene glycol having a molecular weight of about 500 to 1000.

19. A curable epoxy-resin composition according to claim 4, wherein R together with the hydroxyl group has a molecular weight of 100 to 2000.

20. A curable epoxy-resin composition according to claim 4, wherein the diol or polyol is selected from the group consisting of a polyether polyol, a polythioether polyol, a polyacetal polyol and a polyester polyol.

21. A curable epoxy-resin composition according to claim 4, wherein the diol or polyol is polypropylene glycol having a molecular weight of about 500 to 1000.

22. A curable epoxy-resin composition according to claim 7, wherein R together with the hydroxyl group has a molecular weight of 100 to 2000.

23. A curable epoxy-resin composition according to claim 7, wherein the diol or polyol is selected from the group consisting of a polyether polyol, a polythioether polyol, a polyacetal polyol and a polyester polyol.

24. A curable epoxy-resin composition according to claim 7, wherein the diol or polyol is polypropylene glycol having a molecular weight of about 500 to 1000.

* * * * *